United States Patent [19]

Tanaka et al.

[11] Patent Number: 4,886,906

[45] Date of Patent: Dec. 12, 1989

[54] PROCESS FOR PRODUCING 2,6-NAPHTHALENE DICARBOXYLIC ACID

[75] Inventors: Toru Tanaka; Masato Inari, both of Okayama, Japan

[73] Assignee: Mitsubishi Gas Chemical Company, Inc., Tokyo, Japan

[21] Appl. No.: 294,297

[22] Filed: Jan. 6, 1989

[30] Foreign Application Priority Data

Jan. 11, 1988 [JP] Japan ................................. 63-2528

[51] Int. Cl.$^4$ .................... C07B 51/265; C07C 51/245
[52] U.S. Cl. ..................................... 562/416; 502/102; 502/225; 502/324; 502/331; 562/417; 562/421
[58] Field of Search .................... 562/416, 417, 421

[56] References Cited

U.S. PATENT DOCUMENTS 3,856,855  12/1974  Yamashita et al. ................. 562/416

4,764,638  8/1988  Feld ..................................... 562/416

FOREIGN PATENT DOCUMENTS

| | | |
|---|---|---|
| 48-34153 | 5/1973 | Japan . |
| 60-89445 | 5/1985 | Japan . |
| 62-61946 | 3/1987 | Japan . |
| 62-67048 | 3/1987 | Japan . |

Primary Examiner—Werren B. Lone
Assistant Examiner—Vera C. Clarke
Attorney, Agent, or Firm—Browdy and Neimark

[57] ABSTRACT

A process for producing 2,6-naphthalene dicarboxylic acid which comprises oxidizing a 2-alkyl-6-acyl naphthalene with molecular oxygen-containing gas in the presence of a catalyst containing cobalt, manganese, bromine and at least one metal selected from the group consisting of iron, copper and mixtures thereof in an acetic acid solvent is disclosed.

11 Claims, No Drawings

PROCESS FOR PRODUCING 2,6-NAPHTHALENE DICARBOXYLIC ACID

BACKGROUND OF THE INVENTION

This invention relates to a process for producing 2,6-naphthalene dicarboxylic acid (hereinunder referred to as 2,6-NDA) which is useful as a raw material for high quality polyester.

2,6-NDA has been worthy of notice as a raw material for high quality polyester having excellent thermal resistance, mechanical strength, dimensional accuracy and the like. Development of a commercial process for producing 2,6-NDA has been much in demand.

Prior arts on the production of 2,6-NDA are generally of the following three types.

(1) Processes for producing 2,6-NDA which comprise oxidizing 2,6-dimethyl naphthalene in the presence of a catalyst comprising a heavy metal and a bromine compound are disclosed in U.S. Pat. No. 3,856,855 and Japanese Patent Publication (Kokai) No. 34153/1973. In these processes, it is difficult to separate the raw material, 2,6-dimethyl naphthalene from the dimethyl naphthalene mixtures, and the amount of 2,6-dimethyl naphthalene separated is not sufficient.

(2) A process for producing 2,6-NDA which comprises oxidizing 2,6-diisopropyl naphthalene in the presence of a catalyst comprising Co and Mn is disclosed in Japanese Patent Publication (kokai) No. 89445/1985. This process involves use of an excessive amount of the catalyst. So this process is not proper from industrial point of view.

(3) Processes for producing 2,6-NDA which comprise oxidizing a 2-alkyl-6-acyl naphthalene in the presence of a catalyst containing Co and Br or Co, Mn and Br are disclosed in Japanese Patent Publication (kokai) Nos. 61946/1987 and 67048/1987 and U.S. Pat. No. 4,764,638. However, the yield of 2,6-NDA is insufficient in these processes.

Advantageously, 2-alkyl-6-acyl naphthalenes can be easily obtained in a high yield by Friedel Crafts Reaction between commercially available 2-methyl naphthalene and acetyl fluoride or butyryl fluoride. Therefore, 2-alkyl-6-acyl naphthalenes have became remarkable as a raw material for 2,6-NDA.

The present inventors have produced crude 2-methyl-6-butyryl naphthalene from 2-methyl naphthalene, propylene, carbon monoxide and hydrogen fluoride and purified the crude 2-methyl-6-butyryl naphthalene. The inventors have attempted the production of 2,6-NDA from 2-methyl-6-butyryl naphthalene by oxidation under conditions which were known in the prior art. However, high yields of 2,6-NDA cannot be obtained from a 2-alkyl-6-acyl naphthalene in the prior arts.

SUMMARY OF THE INVENTION

The present inventors conducted extensive research on the production of 2,6-NDA from 2-alkyl-6-acyl naphthalene, such as 2-methyl-6-butyryl naphthalene. As a result, we have found that when a co-catalyst comprising an iron compound or copper compound is used together with a catalyst comprising a cobalt compound, a manganese compound and a bromine compound, high yields of 2,6-NDA can be obtained.

This invention relates to a process for producing 2,6-NDA which comprises oxidizing a 2-alkyl-6-acyl naphthalene with molecular oxygen-containing gas in the presence of a catalyst containg cobalt, manganese, bromine and at least one metal selected from the group consisting of iron, copper and mixturees thereof in an acetic acid solvent.

DETAILED DESCRIPTION OF THE INVENTION

Examples of 2-alkyl-6-acyl naphthalenes include 2-methyl-6-acetyl naphthalene, 2-methyl-6-butyryl naphthalene and the like.

Acetic acid used as a solvent may contain small amounts of water formed by a reaction. The reaction mixture is in a slurry state after the reaction. So an adequate amount of acetic acid must therefore be used in order to allow the reaction product to be uniformly dispersed in the acetic acid. Usually, the amount of acetic acid used may be in the range of 2–10 times by weight, preferably 2.5–5 times by weight, of the 2,6-NDA formed.

It is preferably that the cobalt compounds and the manganese compounds used as the catalyst are dissolved in acetic acid under the reaction conditions. Aliphatic carboxylates, halides, oxides, hydroxides, carbonates or acetyl acetate complexes of cobalt or manganese may be used as the cobalt compounds or manganese compounds. The concentration of the cobalt compound in acetic acid may be in the range of 0.06–1.0% by weight and preferably 0.1–0.5% by weight in terms of a cobalt atom. The concentration of the manganese compound in acetic acid may be in the range of 0.06–1.0% by weight and preferably 0.2–1.0% by weight in terms of a manganese atom. If the concentrations of cobalt or manganese are less than 0.06% by weight, the yield of 2,6-NDA is lowered. If the concentrations are more than 1.0% by weight, no increase in the yield of 2,6-NDA is achieved and the extra amount adds unnecessarily to the cost.

Bromine or bromine compounds may be used as the bromine component. Examples of suitable bromine compounds include inorganic bromine compounds, such as hydrobromic acid, sodium bromide, an ammonium bromide and bromides of heavy metals, and organic bromine compounds, such as tetrabromoethane and ethylene bromide. The concentration of the bromine components in acetic acid may be in the range of 0.1–0.8% by weight and preferably 0.1–0.5% by weight in terms of a bromine atom. When the concentration of the bromine component is less than 0.1% by weight, the yield of 2,6-NDA is lowered. If the concentration is more than 0.8% by weight, the solution causes corrosion of the piping and the vessel.

According to the present invention, the iron component and/or the copper component are used as the cocatalyst. The components which are capable of forming metal ion in the reaction system can be used as the co-catalyst. Examples of suitable iron components include iron power, iron chlorides, iron bromides, iron acetates and the like. Examples of suitable copper components include copper powder, copper sulfate, copper acetate, copper chloride, copper bromide and the like. The concentration of the iron component in acetic acid may be in the range of 0.01–0.5% by weight, preferably 0.03–0.1% by weight, in terms of an iron atom. The concentration of the copper component in acetic acid may be in the range of 0.001–0.2% by weight, preferably 0.002–0.05% by weight, in terms of a copper atom. If the concentration of the iron component is less than 0.01% by weight or when the concentration of the copper component is less than 0.001% by weight, the activity of by-reactions is increased and the yield of 2,6-NDA is reduced. If the concentration of the iron component is more than 0.5% by weight or the concentration of the copper component is more than 0.2% by weight, no further increase in the yield of 2,6-NDA is achieved.

Examples of a suitable molecular oxygen-containing gas include air and a mixture of air and oxygen.

The reaction temperature may be in the range of 180° C.–220° C., preferably 200° C.–210° C. If the reaction temperature is higher than 220° C., oxidation of acetic acid proceeds. If the temperature is lower than 180° C., the catalytic action is weakened, and the reactivity is therefore lowered.

The reaction is carried out at a pressure that is high enough to make the reaction system liquid.

The present process can be carried out by (i) a semi continuous method which comprises continuously introducing 2-alkyl-6-acyl naphthalene and the molecular oxygen-containing gas to a solution of the catalyst in acetic acid for a definite time or (ii) a continuous method which comprises continuously introducing the catalyst solution, 2-alkyl-6-acyl naphthalene and molecular oxygen-containing gas into a reaction vessel and continuously discharging the reaction mixture during the reaction.

After the reaction has finished, the reaction mixture is cooled and then crystalline 2,6-NDA is separated from the mixture by a conventional method. When occasion demands, the product is more purified.

This invention is further explained by way of the following non-limiting examples. All percentages are on a weight basis, unless specified otherwise.

EXAMPLE 1

Into a 500 milliliter titanium autoclave equipped with a reflux condenser, an exit for gas, an agitator, an inlet for feeding raw material, an inlet for feeding gas and a heater were charged the following materials:

| acetic acid | 150 gram |
| cobalt acetate tetrahydrate | 1.268 g (Co 0.20%) |
| manganese acetate tetrahydrate | 1.338 g (Mn 0.20%) |
| sodim bromide | 0.966 g (Br 0.50%) |
| iron powder | 0.15 g (Fe 0.10%) |

An nitrogen gas was introduced from the inlet for gas to pressurize the autoclave to 10 Kg/cm$^2$G and then raising the temperature of autoclave to 205° C. The pressure of autoclave was automatically raised to 20 Kg/cm$^2$G. Air was introduced from the inlet for feeding gas to replace the nitrogen with air. The contents were violently stirred while feeding air. 2-methyl-6-butyryl naphthalene which had been previously heated to 60° C. was fed to the autoclave from the inlet during reaction at rate of 0.156 g/min. for 4 hours. After the feeding of 2-methyl-6-butyryl naphthalene was completed, air was supplied for another 10 minutes to complete the oxidation. The autoclave was cooled, depressurized and opened. The cystalline product was obtained by filtering the resulting slurry, was washed with acetic acid and dried. Gas chromatograph analysis of the crystalline product and the filtrate was carried out. As a result, the crystalline product weighed 34.09 g and contained 33.92 g of 2,6-NDA. The filtrate weighted 161.41 g and contained 0.03 g of 2,6-NDA. The yield of 2,6-NDA was 89 mol %.

CONTROL RUN 1

The procedure of Example 1 was repeated except that iron powder was not used. The yield of 2,6-NDA was 72 mol %.

EXAMPLE 2

Into the autoclave of Example 1 were charged the following materials:

| acetic acid | 150 gram |
| cobalt acetate tetrahydrate | 3.17 g (Co 0.50%) |
| manganese acetate tetrahydrate | 3.345 g (Mn 0.50%) |
| sodim bromide | 0.966 g (Br 0.50%) |
| copper powder | 0.015 g (Cu 0.01%) |

An nitrogen gas was introduced from the inlet for gas to pressurize the autoclave to 10 Kg/cm$^2$G and then raising the temperature of autoclave to 205° C. The pressure of autoclave was automatically raised to 20 Kg/cm$^2$G. Air was introduced from the inlet for feeding gas to replace the nitrogen with air. The contents were violently stirred while feeding air. 2-methyl-6-butyryl naphthalene which had been previously heated to 60° C. was fed to the autoclave for reaction at rate of 0.25 g/min. for 2 hours. After the introduction of 2-methyl-6-butyryl naphthalene was completed, air was introduced for another 10 minutes to complete the oxidation. The autoclave was cooled, depressurized and opened. The crystalline product was obtained by filtering and resulting slurry, was washed with acetic acid and dried. Gas chromatograph analysis of the crystalline product and the filtrate was carried out. As a result, the crystalline product weighed 25.98 g and contained 0.34% by weight of the intermediate and impurities. The yield of 2,6-NDA was 85 mol %.

CONTROL RUN 2

The procedure of Example 2 was repeated except that copper powder was not used. The yield of 2,6-NDA was 75 mol %.

EXAMPLE 3

Into a 2 liter zirconium autoclave equipped with a reflux condenser, an exit for gas, an agitator, an inlet for feeding raw material, an inlet for feeding gas, a heater and an exit for reaction product were charged the following materials:

| acetic acid | 750 gram |
| cobalt acetate tetrahydrate | 6.34 g (Co 0.20%) |
| manganese acetate tetrahydrate | 6.69 g (Mn 0.20%) |
| ferrous bromide | 1.01 g (Fe 0.10%) |
| 47% hydrobromic acid solution | 9.02 g (Br 0.60%) |

An nitrogen gas was introduced into the autoclave under pressure; and the autoclave was heated to 210° C. Then air is introduced into the autoclave with stirring. The mixture of the catalyst solution and 2-methyl-6-butyryl naphthalene (ratio of 3:1) was continuously supplied into the autoclave at rate of 500 g/hour and at the same time the slurry containing the resulting product was continuously discharged from the autoclave. The operation was continued for 5 hours so that liquid level in the autoclave was kept constant. After the supplying of the mixture was finished, air was fed further into the autoclave for another 10 minutes to complete the oxidation.

The reaction mixture was treated in the same way as in Example 1. The yield of 2,6-NDA was 87.5 mol % and the purity thereof was 99.5%.

CONTROL RUN 3

Into the autoclave of Example 3 were charged the following materials:

| | |
|---|---|
| acetic acid | 750 gram |
| cobalt acetate tetrahydrate | 7.93 g (Co 0.25%) |
| manganese acetate tetrahydrate | 8.36 g (Mn 0.25%) |
| ferrous bromide | 1.21 g (Fe 0.12%) |
| 47% hydrobromic acid solution | 6.07 g (Br 0.50%) |
| 2-methyl-6-butyryl naphthalene | 171.9 g |

An nitrogen gas was introduced from the inlet for gas to pressurize the autoclave to 20 Kg/cm$^2$G. The temperature of autoclave was raised to 205° C. Then air was fed into the autoclave from the inlet for gas and the agitation was increased. The temperature of autoclave was rapidly raised to 223° C.; and the concentration of oxygen in the waste gas was decreased to 0.05%. After the state was continued for 5 minutes, the oxygen concentration in the waste gas gradually increased and the temperature was gradually lowered. After 12 minutes passed, the oxygen concentration amounted to 14% and the temperature amounted to 215° C.

The reaction further proceeded. When finally the oxygen concentration amount to 20%, the introduction of air was discontinued. The reaction mixture was treated in the same was as in Example 1.

The colour of reaction product was red-brown. The yield of 2,6-NDA was 67 mol %. When 2,6-NDA was produced by a batch method, the addition of Fe did not allow the yield of 2,6-NDA to be increased.

EXAMPLES 4–10 AND CONTROL RUNS 4–9

The procedures of Example 3 were repeated except that the components and the reaction conditions given in Table 1 were used. The results are shown in Table 1.

According to this invention, 2-alkyl-6-acyl naphthalene can be easily prepared in a high yield by reacting commercially available 2-methyl naphthalene with acetyl fluoride or butyryl fluoride due to Friedel Crafts Reaction. Therefore, industrial significance of this invention is great.

What is claimed is:

1. A process for producing 2,6-naphthalene dicarboxylic acid which comprises oxidizing a 2-alkyl-6-acyl naphthalene with molecular oxygen-containing gas in the presence of a catalyst containing cobalt, manganese, bromine and at least one metal selected from the group consisting of iron, copper and mixtures thereof in an acetic acid solvent, the concentration of cobalt in the acetic acid solvent being in the range of 0.06–1% by weight, the concentration of manganese in the acetic acid solvent being in the range of 0.06–1.0% by weight and the concentration of bromine being in the range of 0.1–0.8% by weight; and when iron is used, the concentration of iron being in the range of 0.01–0.5% by weight; and when copper is used, the concentration of copper being in the range of 0.001–0.2% by weight, these percentages being in terms of elements.

2. The process of claim 1 where the process is continuously or semi-continuously carried out.

3. The process of claim 2 wherein the concentration of cobalt in the acetic acid solvent is in the range of 0.1–0.5% by weight.

4. The process of claim 1 wherein the concentration of manganese in the acetic acid solvent is in the range of 0.2–1.0% by weight.

5. The process of claim 1 wherein the concentration of bromine in the acetic acid solvent is in the range of 0.1–0.5% by weight.

6. The process of claim 1 wherein the concentration of iron in the acetic acid solvent is in the range of 0.03–0.1% by weight.

7. The process of claim 1 wherein the concentration of copper in the acetic acid solvent is in the range of 0.002–0.05% by weight.

8. The process of claim 1 wherein the amount of acetic acid used is in the range of 2–10 times by weight of the 2,6-naphthalene dicarboxylic acid formed.

9. The process of claim 1 wherein the amount of acetic acid used is in the range of 2.5–5 times by weight of the 2,6-naphthalene dicarboxylic acid.

10. The process of claim 1 wherein the reaction is carried out at a temperature of 180°–220° C.

11. The process of claim 1 wherein the reaction is carried out at a temperature of 200°–210° C.

TABLES

| No. | | Concentration in catalyst solution (weight % in acetic acid) | | | | reaction temperature (°C.) | ratio of catalyst solution to raw material (by weight) | feed rate of catalyst solution and raw material (g/hrs) | residence time (hour) | yield of 2,6-NDA mol % |
|---|---|---|---|---|---|---|---|---|---|---|
| | Co | Mn | Br | Fe | Cu | | | | | |
| Ex. 4 | 0.75 | 0.75 | 0.50 | 0.40 | — | 205 | 3 | 500 | 2.0 | 85.5 |
| 5 | 0.15 | 0.35 | 0.30 | 0.10 | — | 210 | 7 | 500 | 2.0 | 89.6 |
| 6 | 0.15 | 0.75 | 0.85 | — | 0.05 | 200 | 7 | 500 | 2.0 | 90.2 |
| 7 | 0.50 | 0.50 | 0.30 | — | 0.005 | 205 | 5 | 750 | 1.0 | 88.7 |
| 8 | 0.25 | 0.75 | 0.55 | 0.05 | — | 210 | 5 | 750 | 1.0 | 84.7 |
| 9 | 0.75 | 0.75 | 0.85 | — | 0.10 | 215 | 10 | 350 | 3.5 | 85.1 |
| 10 | 0.35 | 0.35 | 0.50 | 0.02 | — | 200 | 3 | 500 | 2.0 | 88.4 |
| Cont. Run 4 | 0.50 | 0.75 | 0.30 | 0.65 | — | 215 | 5 | 750 | 1.0 | 76.6 |
| 5 | 0.90 | 0.90 | 0.50 | — | 0.30 | 215 | 7 | 500 | 2.0 | 77.9 |
| 6 | 0.50 | 0.35 | 0.45 | 0.005 | — | 200 | 3 | 500 | 2.0 | 74.2 |
| 7 | 0.20 | 0.20 | 0.50 | — | 0.0005 | 205 | 5 | 750 | 1.0 | 71.8 |
| 8 | 0.05 | 0.05 | 0.07 | 0.15 | — | 210 | 5 | 750 | 1.0 | 70.4 |
| 9 | 1.50 | 1.50 | 2.50 | — | 0.01 | 210 | 7 | 500 | 2.0 | 73.5 |